United States Patent [19]

McRae

[11] Plant 5,006

[45] Mar. 22, 1983

[54] LILY PLANT: LILIUM INFERNO

[75] Inventor: Edward A. McRae, Boring, Oreg.

[73] Assignee: Melridge, Inc., Sandy, Oreg.

[21] Appl. No.: 200,968

[22] Filed: Oct. 27, 1980

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Eugene D. Farley

[57] ABSTRACT

A new variety of Asiatic hybrid lily plant bearing large clusters of medium-sized flowers of excellent form, unusual color, and long persistence, both on the plant and as cut flowers. The plant is characterized by rapid natural propagation under field conditions, vigorous and healthy growth when forced under glass, unusually rapid growth to its flowering stage when forced under glass, high resistance to disease and virus, and in particular by the brilliant orange color of its flower with virtually no spots.

1 Drawing Figure

BACKGROUND AND GENERAL STATEMENT OF THE INVENTION

My new variety of lily plant is classified botanically as a Lilium hybrid. It is classified commercially as an upright Asiatic hybrid, division I-A in the Horticultural Classification of the Genus Lilium adopted by The Royal Horticultural Society of London.

My new variety of lily plant originated as a seedling selected from a group of seedlings at Oregon Bulb Farms, Sandy, Oreg.

The seedlings were planted during a breeding program carried on by me since the year 1965. This program has as its primary objectives the production of brilliantly-colored, unspotted or scarcely spotted, upright-flowering lily cultivars which will perform well when forced into flower under glass throughout the year, in addition to meeting the requirements of vigor, disease resistance, and rapid natural propagation in field cultivation. Cultivars are sought which will be disease resistant, virus tolerant, and not unduly susceptible to leaf scorch or bud abortion when forced under glass.

My new variety of lily plant resulted from a cross made in 1968 between its seed parent 'Cinnabar' (not patented) and its pollen parent 'Red Carpet' (not patented). The plant first flowered in 1970 among the seedling beds of test crosses at Oregon Bulb Farms.

My new lily plant shows vigorous growth and propagation characteristics. It is characterized by rapid natural propagation under field conditions and also by vigorous and healthy growth when forced under glass. When forced under glass it is not subject to excessive leaf scorch or bud abortion.

When forced under glass my new lily plant is further characterized by unusually rapid growth to its flowering stage. It is highly resistant to diseases and tolerant to virus.

In particular, my new lily plant is characterized by the brilliant orange color of its flowers. Since its flowers have virtually no spots, this color is unusually deep and rich.

My new lily plant most closely resembles Lilium 'Enchantment'; U.S. Plant Pat. No. 862. However, it has virtually no spots so that the color is richer and deeper. It also flowers more rapidly when forced, requiring seven to ten days fewer than 'Enchantment' to reach flowering stage when forced. This makes it of particular value as a cut flower cultivar.

My new variety of lily plant has been asexually reproduced by me and under my direction at Sandy, Oreg. It is propagated by scale propagation and natural vegetative increase (bulb division). Successive generations have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows the plant, its foliage, its buds in their various stages of development, and the open bloom in full color.

DETAILED DESCRIPTION OF THE NEW VARIETY

The following is a detailed description of Lilium 'Inferno', with nomenclature according to the *International Lily Register* (Horticultural Society of London, Second Edition, 1969) and with color designations according to The Royal Horticultural Society Color Chart, published by The Royal Horticultural Society in 1966.

THE PLANT

Form: Bulbous monocotyledon.
Height: 66–86 cm. (26–34") at maturity (second year) from 15–18 cm. circumference bulb.
Growth: Vigorous, with considerable strength.
Foliage: Abundant, about 80 to 100 leaves per stem.
Size of leaves: 7–9 cm. (3–4") long and 1 cm. (½") broad.
Shape of leaves: Broad lanceolate.
Texture of leaves: Leaves entire, not serrated, glossy, smooth-surfaced, with lightly pubescent margins.
Color of leaves, upperside: Deep glossy green.
Color of leaves, underside: Medium glossy green, with pink overcast under unusually cool conditions.
Rubs and veins of leaves: Typical monocotyledonous venation; light green parallel veins.
Blooms late June or July in Western Oregon, once, in mid-season and profusely.
Color of bulbs: White.

Size of bulbs: Usual commercial size is 12–20 cm. (5–8") in circumference; bulbs can reach much larger size, if desired, under continued cultivation.

INFLORESCENCE

Compact raceme: Bulbs 12–15 cm. in circumference produce about 8–12 buds. Influorescence does not carry secondary buds.

Peduncle and pedicels not hairy.

Strength of inflorescence: Strong and wirey.

Color of inflorescence: Dark green stems overlaid with maroon anthocyanin pigment; buds brilliant orange.

THE BUD

Size: 7–9 cm. (3–3½") long.

Form: Lanceolate with obtuse tips; typical of Asiatic lily hybrids.

Opens slowly: Opens in about 1 hour in response to morning light; flowers further up the stem open on subsequent days over an interval of 1–2 weeks. Typical of upright Asiatic hybrid lilies.

Color of mature buds: Brilliant orange, R.H.S. CC #28A-B.

THE FLOWER

Blooms: Late June or early July in western Oregon, once, in mid-season, and profusely.

Size:

*Flower diameter.*—15–18 cm. (6–7").

*Inner tepals.*—3 cm (1¼") wide.

*Outer tepals.*—2.5 cm (1") wide.

Shape when flower first opens: Bowl-shaped with slightly recurving tepals.

Tepals recurve more as flower ages.

The illustrated color is less orange than the actual color, in view of the lighting condition at the time the blossoms were photographed. The variety, Enchantment, shows the true orange color, but with less intensity.

Tepal arrangement: Typical of genus Lilium, with six entire, imbricated tepals.

*Color, outer tepal.*—Glowing brilliant orange, 28-A on the Color Code of the Royal Horticultural Society of London.

*Color, base of tepals.*—Brilliant orange, R.H.S. CC #28A; midrib is R.H.S. CC #30A.

*Color, inner tepal.*—Brilliant orange, R.H.S. CC #30A.

*Color, reverse of tepal.*—Brilliant orange, R.H.S. CC #30A-B.

Tepals remain on individual flowers 5–7 days; stem has flowers with tepals adhering for about 3 weeks.

Flower texture: Shiny, velvety. Is not affected by hot or wet weather.

*Persistence.*—It does not hang on and dry; tepals fall as flower ages.

Pedicels: 4–6 cm (1½–2½") long. Sturdy and upright.

*Color.*—Dark green, overlaid with reddish-maroon anthocyanin pigment.

Disease resistance: To Botrytis blight and to Fusarium bulb rot.

Fragrance: None

Lasting quality: Flowers remain on plants for about 3–4 weeks. Flowers remain on cut-flower stems for 2 to 3 weeks, with adequate light.

THE REPRODUCTIVE ORGANS

Stamens and anthers: Typical of genus Lilium. Six versatile anthers hang (singly) from six filaments.

Filaments: 5–6 cm (2") long and light reddish-orange.

Pollen: Deep golden brown.

Pistil: 1, typical of genus Lilium. Style is 5–6 cm (2") long.

Stigma: Tiny, three-lobed, dark plum in color, velvety texture.

Ovary: Typical of genus Lilium. Superior, single, 6-chambered ovary.

THE FRUIT

Fertile, an ovoid to oblong capsule with six chambers.

Color at maturity: Medium green overlaid with purple; fades to soft brown when fruit splits open to release seeds.

I claim:

1. A new and distinctive variety of Asiatic hybrid lily plant substantially as herein shown and described characterized by its rapid natural propagation under field conditions, its vigorous and healthy growth when forced under glass, its unusually rapid growth to its flowering stage when forced under glass, its resistance to disease and virus, and the brilliant orange color of its flowers, with virtually no spots.

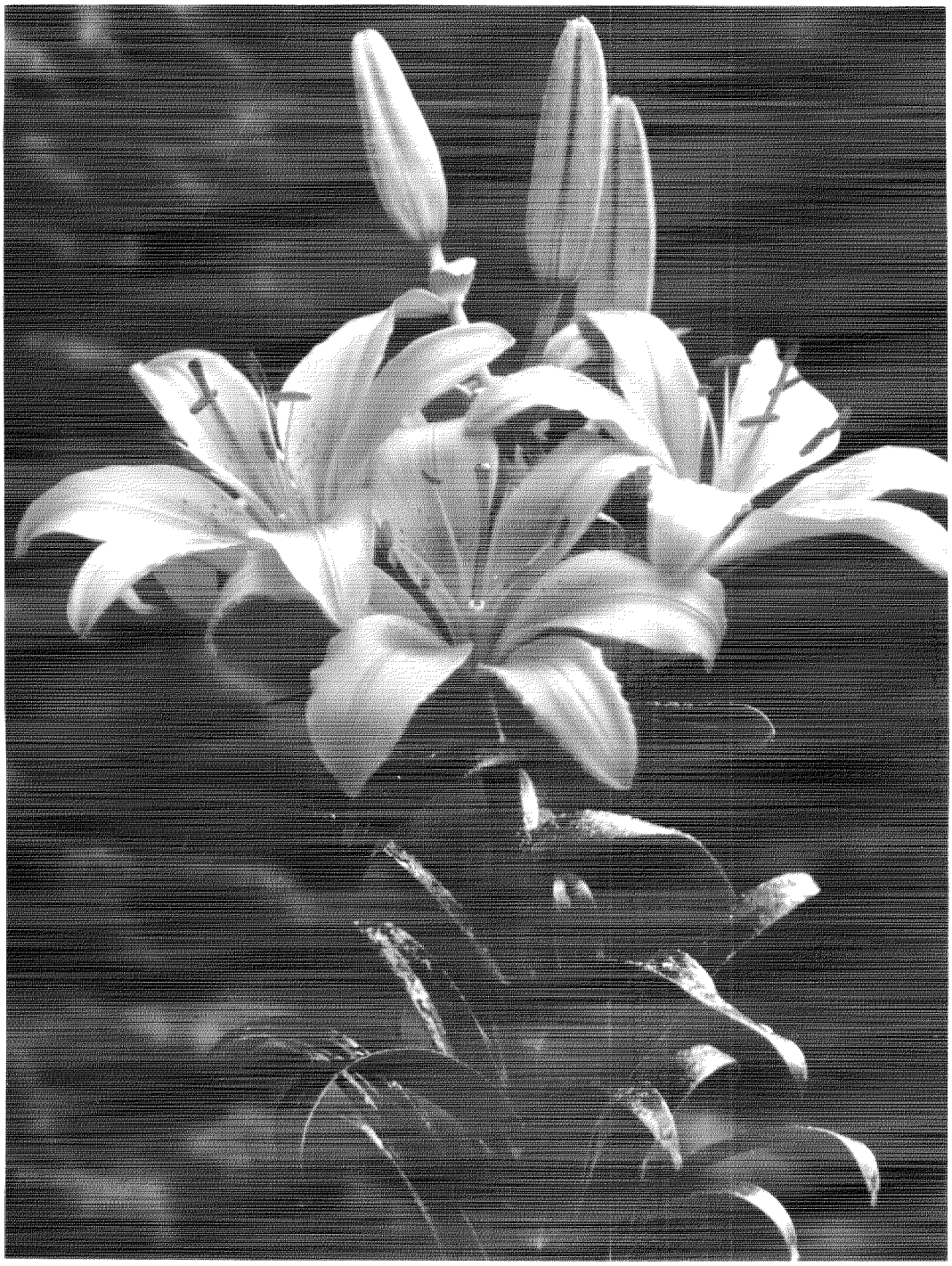

* * * * *